(12) United States Patent
Satoh et al.

(10) Patent No.: US 11,147,834 B2
(45) Date of Patent: Oct. 19, 2021

(54) COMPOSITION FOR TREATMENT OR PREVENTION OF AGE-RELATED MACULAR DEGENERATION COMPRISING MOLECULAR HYDROGEN

(71) Applicant: MiZ Company Limited, Kanagawa (JP)

(72) Inventors: Fumitake Satoh, Kanagawa (JP); Shinichi Hirano, Kanagawa (JP); Yusuke Ichikawa, Kanagawa (JP); Takeshirou Takekoshi, Niigata (JP)

(73) Assignee: MIZ COMPANY LIMITED, Kanagawa (JP)

( * ) Notice: Subject to any disclaimer, the term of this patent is extended or adjusted under 35 U.S.C. 154(b) by 53 days.

(21) Appl. No.: 16/428,324

(22) Filed: May 31, 2019

(65) Prior Publication Data
US 2019/0388462 A1    Dec. 26, 2019

(30) Foreign Application Priority Data

Jun. 1, 2018   (JP) .............................. JP2018-106428

(51) Int. Cl.
A61K 33/00 (2006.01)
A61K 9/00 (2006.01)
A61P 27/02 (2006.01)

(52) U.S. Cl.
CPC .............. *A61K 33/00* (2013.01); *A61K 9/007* (2013.01); *A61P 27/02* (2018.01)

(58) Field of Classification Search
CPC .................................................... A61P 27/02
See application file for complete search history.

(56) References Cited

U.S. PATENT DOCUMENTS

2020/0281963 A1* 9/2020 Takahashi .............. A61K 33/00

FOREIGN PATENT DOCUMENTS

WO   WO-2017126708 A1 *  7/2017 ............. A61K 33/00

OTHER PUBLICATIONS

Koto T. Keio Associated Repository of Academic Resources, 2012, "Effect of hydrogen gas in the age-related macular degeneration," document and partial translation provided by the applicant; see PTO-1449 dated Sep. 11, 2019. (Year: 2012).*
B. S. Winkler, M. E. Boulton, J. D. Gottsch, and P. Sternberg. "Oxidative damage and age-related macular degeneration," Mol. Vis., 5: 32, Nov. 1999, 1-27. (Year: 1999).*
Google search Feb. 10, 2021 (Year: 2021).*
Google scholar search Feb. 10, 2021 (Year: 2021).*
Takashi Koto, Keio Associated Repository of Academic Resources, 2012, "Effect of hydrogen gas in the age-related macular degeneration" (with Partial Translation).
L. Tian et al., "Hydrogen-rich saline ameliorates the retina against light-induced damage in rats", Medical Gas Research, 3:19 (2013).
Ohno, K., "Scientific Bases of Molecular Hydrogen," *Anti-Aging Medicine*, 7(3):378-387 (2011) (in Japanese and including English translation of the Summary on p. 378).
Ohta, S., "Current Status of Hydrogen Medicine: From Basic Medicine to Clinical Medicine," *Pharmacia*, 48(8):767-771 (2012) (in Japanese and including English translation of the Introduction on p. 767, lines 1-9).
Qi, L-S., et al., "Sirtuin Type 1 Mediates the Retinal Protective Effect of Hydrogen-Rich Saline Against Light-Induced Damage in Rats," *Retinal Cell Biology, IOVS*, 56(13):8268-8279 (Dec. 2015).

* cited by examiner

*Primary Examiner* — Michael P Cohen
(74) *Attorney, Agent, or Firm* — Crowell & Moring LLP

(57) ABSTRACT

The present application provides a composition for treatment or prophylaxis of age-related macular degeneration in a subject, comprising molecular hydrogen as an active ingredient, and a method for treatment or prophylaxis of age-related macular degeneration, comprising administering the composition to a subject with age-related macular degeneration.

5 Claims, No Drawings

COMPOSITION FOR TREATMENT OR PREVENTION OF AGE-RELATED MACULAR DEGENERATION COMPRISING MOLECULAR HYDROGEN

RELATED APPLICATIONS

The present patent document claims priority to Japanese Patent Application No. JP 2018-106428, filed Jun. 1, 2018, which is hereby incorporated by reference.

FIELD OF THE INVENTION

The present invention relates to treatment, amelioration, or prophylaxis (or prevention) of age-related macular degeneration by using molecular hydrogen.

BACKGROUND ART

Age-related macular degeneration (AMD) is a disease having macular disorder accompanied by aging (e.g., 50 years old or more). AMD is the (fourth, in 2018) leading cause of visual loss in Japan. The macular is at the center of the retina and is an important part where photoreceptor cells are concentrated. AMD refers to late-stage age-related maculopathy when broadly classified as age-related maculopathy (ARM) and is classified into wet AMD and dry AMD (Non Patent Literatures 1 and 2). In wet AMD, as aging of retinal pigment epithelial cells progresses, vascular endothelial growth factor (VEGF) is secreted in excess and inflammatory cytokines are produced, etc., resulting in choroidal neovascularization under the macular choroid or the retina. In addition, the neovascularization causes retinal pigment epithelium detachment and/or retinal hemorrhage. Consequently, the disease is responsible for seriously reduced visual acuity. By contrast, dry AMD is not accompanied by choroidal neovascularization and the macular part has an atrophic lesion of pigment epithelium and choroidal capillary layer formed therein. Accordingly, the disease progression is relatively slow. When dry AMD progresses, this causes geographic atrophy. Also, it is said that, in the geographic atrophy, in which the other eye has choroidal neovascularization, choroidal neovascularization is likely to develop.

It has been known that the onset of AMD is correlated with versatile genetic and environmental factors. Here, aging is a determined risk factor. Further, it has been reported that oxidative stress participates in AMD pathogenesis (Non Patent Literatures 1 to 4). Oxidative stress generally refers to a process in which reactive oxygen species (ROS) generated through a metabolic process in a tissue damage cells. ROS, by themselves, damage cell membranes and/or genes, promote expression of ischemia-related molecules, and oxidize lipids, etc. Thus, ROS cause harmful effects in vivo. The photoreceptor outer segment is basically very rich in lipids. In addition, aging causes lipids to accumulate also in Bruch's membrane. Hence, it can be said that the outer layer of the retina is susceptible to oxidative stress damage (Non Patent Literature 1).

In the case of wet AMD, examples of a clinical therapeutic drug for AMD include anti-VEGF drugs (e.g., ranibizumab, bevacizumab, aflibercept). Each drug is used for treatment and has an effect of suppressing VEGF-mediated angiogenesis. In addition, in the case of dry AMD, drugs such as an anti-inflammatory drug and a choroidal blood flow enhancer are being used in clinical practice. However, no effective treatment protocol has been established. Further, when an anti-VEGF drug alone should not improve visual acuity, performed are a surgery for removal of choroidal neovascularization, a surgery for removing hematoma, and/or a photodynamic therapy for targeted occlusion of neovascularization, etc. (Non Patent Literature 1).

Furthermore, cell therapy has increasingly been performed on patients with wet AMD, in which an autologous iPS cell-derived retinal pigment epithelial cell sheet is transplanted in the retina (Non Patent Literature 5).

Regarding a molecular hydrogen-mediated effect on AMD, a report (Non Patent literature 6) said that a tiny amount of hydrogen water (0.3 µg) was preliminary administered (via gavage) prior to laser irradiation to mice, which were a laser-guided choroidal neovascularization treatment model; but because the level of reactive oxygen in mice was too high, the tiny amount of hydrogen was not enough to scavenge the reactive oxygen; and thus the formation of choroidal neovascularization could not significantly be suppressed. Moreover, it has been reported (in Non Patent Literature 7) that hydrogen-rich saline can reduce rat retinal damage caused by photoirradiation. Nevertheless, treatment efficacy of hydrogen on AMD is unknown.

CITATION LIST

Non Patent Literature

[Non Patent Literature 1] Edited by Nagahisa Yoshimura, Age-related Macular degeneration, 2nd edition (2016), Igaku-Shoin Ltd., Tokyo, Japan.

[Non Patent Literature 2] Edited by Tatsuro Ishibashi, Age-related Macular Degeneration <NEW Mook Ophthalmology, No. 9>, 1st ed. (2005), KANEHARA & Co., LTD., Tokyo, Japan.

[Non Patent Literature 3] Hiroshi Kunikata and Toni Nakazawa, Jikken Igaku Vol. 36, No. 5 (special issue), page 199 to 204, "16. Eye Disease and Oxidative Stress", 2018, YODOSHA CO., LTD., Tokyo, Japan.

[Non Patent Literature 4] Supervised by Toshikazu Yoshikawa, Medicine on Oxidative Stress, revised, 2nd ed. (2014), page 272 to 277, "Section 3: Eye Disease and Oxidative Stress", SHINDAN TO CHIRYO SHA, Inc., Tokyo, Japan.

[Non Patent Literature 5] Michiko Mandai et al., "Autologous Induced Stem-Cell-Derived Retinal Cells for Macular Degeneration", The New England Journal of Medicine, 2017; 376: 1038-1046.

[Non Patent Literature 6] Takashi Koto, Keio Associated Repository of Academic Resources, 2012, "Effect of hydrogen gas in the age-related macular degeneration". http://koara.lib.keio.ac.jp/xoonips/modules/xoonips/detail.php?koara_id=KAKEN_2 2791688seika

[Non Patent Literature 7] L. Tian et al., Medical Gas Research 2013, 3: 19.

SUMMARY OF THE INVENTION

Technical Problem

Age-related macular degeneration is still refractory disease in which existing treatment is insufficient for amelioration and/or remission. It is difficult to remove a genetic factor responsible for AMD. However, for prophylaxis of AMD against environmental factors, it is recommended to intake anti-oxidant supplement, quit smoking, prevent UV light, and manage blood pressure, etc. In addition, as stated above, in clinical practice, a surgery and/or a drug therapy for suppressing angiogenesis in patients with wet AMD as well as cell therapy are implemented. However, a further advanced treatment technology should be sought for sufficient improvement.

In addition, to date, the therapeutic effect of molecular hydrogen on AMD has not been verified (Non Patent Literature 6).

Solution to Problem

Surprisingly, the present inventors have lately discovered that hydrogen therapy exerts a drastic effect of ameliorating age-related macular degeneration (AMD).

Thus, the present invention includes the following features.

(1) A composition for treatment or prophylaxis of age-related macular degeneration in a subject, comprising molecular hydrogen as an active ingredient.

(2) The composition according to the above (1), wherein the composition is in a form of hydrogen gas-containing gas and/or hydrogen-dissolved liquid.

(3) The composition according to the above (2), wherein a hydrogen concentration in the hydrogen gas-containing gas is from 0.5 to 18.5% by volume.

(4) The composition according to the above (2), wherein a hydrogen concentration in the hydrogen-dissolved liquid is from 1 to 10 ppm.

(5) The composition according to any of the above (1) to (4), wherein when the composition is administered to the subject, the administration is transpulmonary administration, intravenous administration, intraocular administration, or oral administration.

(6) The composition according to the above (5), wherein the transpulmonary administration is carried out under an atmospheric pressure condition or under a high-pressure condition at from 1.02 to 7.0 atm.

(7) The composition according to any of the above (1) to (6), wherein the composition is prepared in situ at the time of administration to the subject by using a hydrogen gas generator, a hydrogen water generator, or a hydrogen gas-adding apparatus.

(8) The composition according to any of the above (1) to (7), wherein the age-related macular degeneration is age-related macular degeneration that causes choroidal angiogenesis.

(9) The composition according to any of the above (1) to (8), wherein the composition is used in combination with another drug for treatment of age-related macular degeneration.

(10) The composition according to the above (9), wherein another drug for treatment of age-related macular degeneration is an anti-angiogenic drug.

(11) The composition according to the above (9), wherein another drug for treatment of age-related macular degeneration is an antioxidant.

(12) The composition according to any of the above (1) to (11), wherein the subject is a human.

(13) A method for treatment or prophylaxis of age-related macular degeneration in a subject with age-related macular degeneration, comprising administering, to the subject, the composition according to any of the above (1) to (12).

Effect of the Invention

According to the present invention, simple hydrogen therapy is implemented on patients with AMD; this therapy causes choroidal neovascularization to substantially disappear without any adverse events and also causes retinal pigment epithelium detachment to be substantially lost, resulting in providing excellent advantageous effects of dramatically improving visual acuity.

MODES FOR CARRYING OUT THE INVENTION

The following further describes, in detail, the present invention.

1. Age-Related Macular Degeneration (AMD)

As used herein, the "age-related macular degeneration" (sometimes referred to as "AMD") refers to one or both of wet age-related macular degeneration (sometimes referred to as "wet AMD") and dry age-related macular degeneration (sometimes referred to as "dry AMD").

As described in the above Description of the Related Art, in wet AMD, as aging of retinal pigment epithelial cells progresses, vascular endothelial growth factor (VEGF) is secreted in excess and inflammatory cytokines are produced, etc., resulting in choroidal neovascularization under the macular choroid or the retina. In addition, in wet AMD, the neovascularization causes retinal pigment epithelium detachment and/or retinal hemorrhage. Consequently, the disease is responsible for seriously reduced visual acuity.

Dry AMD is not accompanied by choroidal neovascularization and the macular part has an atrophic lesion of pigment epithelium and choroidal capillary layer formed therein. Accordingly, the disease progression is relatively slow. However, when dry AMD progresses, this causes geographic atrophy. Also, it is said that, in the geographic atrophy, in which the other eye has choroidal neovascularization, choroidal neovascularization is likely to develop.

To date, it has not been reported that molecular hydrogen is effective in treatment of AMD. Here, the present invention is characterized in that a composition for treatment or prophylaxis of AMD comprises molecular hydrogen as an active ingredient. The composition of the present invention can cause choroidal neovascularization, which is a main disease pathology of AMD, to substantially disappear and retinal pigment epithelium detachment to be substantially lost, thereby capable of markedly improving visual acuity of AMD patents. Hence, the present invention can be effectively used for treatment or prophylaxis of AMD (e.g., wet AMD) that causes choroidal angiogenesis.

2. Molecular Hydrogen-Containing Composition for Treatment or Prophylaxis of Age-Related Macular Degeneration A first aspect of the present invention provides a composition for treatment or prophylaxis of age-related macular degeneration (AMD) in a subject, comprising molecular hydrogen as an active ingredient.

As used herein, the "hydrogen", which is an active ingredient of the composition for treatment or prophylaxis of AMD according to the present invention, refers to molecular hydrogen (i.e., gaseous hydrogen). Unless otherwise indicated, the "hydrogen" may be sometimes simply referred to as "hydrogen" or "hydrogen gas". In addition, as used herein, the term "hydrogen" has a molecular formula of $H_2$, $D_2$ (deuterium), or HD (hydrogen deuteride), or refers to a mixed gas thereof. Although expensive, it has been known that $D_2$ has a stronger superoxide-scavenging action than $H_2$. The hydrogen that can be used in the present invention is $H_2$, $D_2$ (deuterium), HD (hydrogen deuteride), or a mixed gas thereof, and preferably $H_2$. Alternatively, instead of $H_2$ or by mixing with $H_2$, $D_2$ and/or HD may be used.

A preferable form of composition according to the present invention is a form of hydrogen gas-containing gas and/or hydrogen-dissolved liquid.

The hydrogen gas-containing gas is preferably hydrogen gas-containing air or a mixed gas containing hydrogen gas and oxygen gas. The concentration of hydrogen gas in the hydrogen gas-containing gas is more than zero (0) and 18.5% by volume or less, for instance, 0.5 to 18.5% by volume, 1 to 10% by volume, 2 to 10% by volume, 2 to 8% by volume, 3 to 10% by volume, 3 to 8% by volume, 3 to 7% by volume, 3 to 6% by volume, 4 to 10% by volume, 4 to 8% by volume, 4 to 7% by volume, 4 to 6% by volume, 4 to 5% by volume, 5 to 10% by volume, 5 to 8% by volume, or 5 to 7% by volume, etc.

Because hydrogen is flammable and explosive gas, it is preferable in treatment of AMD to administer, to a subject, a composition for treatment or prophylaxis obtained by including hydrogen under conditions that are safe for subjects such as humans. To achieve this, it is desirable to use the devices such as a hydrogen gas generator as described later.

If the gas other than hydrogen gas is air, the concentration of air ranges, for instance, from 81.5 to 99.5% by volume.

If the gas other than hydrogen gas is oxygen gas-containing gas, the concentration of oxygen gas ranges, for instance, from 21 to 99.5% by volume.

Nitrogen gas, as other chief gas, may be included. Gas such as carbon dioxide, which is gas contained in the air, may be included in an amount that is about the level of abundance in the air.

The hydrogen-dissolved liquid is specifically an aqueous liquid in which hydrogen gas is dissolved. Here, examples of the aqueous liquid include, but are not limited to, sterilized water, saline, buffers (e.g., buffers at pH 4 to 7.4), ethanol-containing water (e.g., ethanol content is from 0.1 to 2% by volume), instillation fluids, infusion liquids, eye drops, injection solutions, and beverages. The hydrogen concentration in the hydrogen-dissolved liquid is, for instance, 1 to 10 ppm, 1.2 to 8 ppm, 1.5 to 7 ppm, 1.5 to 5 ppm, 2 to 10 ppm, 3 to 10 ppm, 4 to 10 ppm, 5 to 10 ppm, or 6 to 10 ppm.

Another drug for treatment of age-related macular degeneration (e.g., an anti-angiogenic drug and an antioxidant) may be added to the hydrogen-dissolved liquid as necessary. Examples of the anti-angiogenic drug include anti-VEGF drugs (e.g., ranibizumab, bevacizumab, aflibercept) and steroid medicines (adrenocortical hormone such as triamcinolone acetonide). Examples of the antioxidant include vitamin A, vitamin C or E, carotenoids, polyphenols, luteins, anthocyanin, zeaxanthin, and zinc. Examples of the other drugs include docosahexaenoic acid (DHA) and eicosapentaenoic acid (EPA), which are considered to suppress the onset of AMD.

The hydrogen gas-containing gas or the hydrogen-dissolved liquid is prepared to have a predetermined concentration of hydrogen gas. Then, either is charged into, for instance, a pressure-resistant container (e.g., a stainless steel cylinder, aluminum can, preferably a pressure-resistant plastic bottle (e.g., a pressure-resistant PET bottle), a plastic bag, and an aluminum bag having an aluminum film lamination on the inner side). Aluminum is characterized in that hydrogen molecules are hard to permeate. Meanwhile, the hydrogen gas-containing gas or the hydrogen-dissolved liquid is characterized in that hydrogen itself is easy to be lost. Preferably, either may be prepared in situ at the time of administration by using a hydrogen gas generator, a hydrogen water generator, or a hydrogen gas-adding apparatus, for instance, each device such as a known or commercially available hydrogen gas supply device (device for generating hydrogen gas-containing gas), a hydrogen-adding instrument (device for generating hydrogen water), or a nondestructive hydrogen-adding apparatus (e.g., an apparatus for adding, in a nondestructive manner, hydrogen gas to the inside of a bag for biocompatible liquid such as instillation fluid).

The hydrogen gas supply device makes it possible to mix, at a predetermined ratio, diluent gas (e.g., the air and oxygen) and hydrogen gas generated by reacting water with a hydrogen generating agent (e.g., metallic aluminum and magnesium hydride) (Japanese Patent No. 5228142, etc.). Alternatively, hydrogen gas generated by using electrolysis of water is mixed with diluent gas such as oxygen or the air (Japanese Patent No. 5502973, Japanese Patent No. 5900688, etc.). This makes it possible to prepare hydrogen gas-containing gas at a hydrogen concentration within a range from 0.5 to 18.5% by volume.

The hydrogen-adding instrument is a device for generating hydrogen by using a hydrogen generating agent and a pH modifier and dissolving the hydrogen into a biocompatible liquid such as water (Japanese Patent No. 4756102, Japanese Patent No. 4652479, Japanese Patent No. 4950352, Japanese Patent No. 6159462, Japanese Patent No. 6170605, Japanese Patent Laid-Open No. 2017-104842, and Japanese Patent No. 6159462, etc.). Examples of the combination of a hydrogen generating agent and a pH modifier include metallic magnesium and strong acid ion-exchange resin or organic acid (e.g., malic acid, citric acid), and metallic aluminum powder and calcium hydroxide powder. This makes it possible to prepare hydrogen-dissolved liquid at a concentration of dissolved hydrogen of about 1 to 10 ppm (e.g., trade name "7 WATER" (Quasia, Inc.)).

The nondestructive hydrogen-adding apparatus is an apparatus or instrument for adding, from the outside of a package, hydrogen molecules to a commercially available biocompatible liquid, like instillation fluid, (e.g., contained in a hydrogen-permeable plastic bag such as a polyethylene bag) and has been marketed by, for instance, MiZ Company Limited (www.e-miz.co.jp/technology.html). This apparatus has the biocompatible liquid-containing bag soaked in hydrogen-rich water, thereby capable of aseptically dissolving hydrogen into the biocompatible liquid until the hydrogen permeates into the bag and the concentration reaches equilibrium. This apparatus includes, for instance, an electrolyzer and a water tank. Water in the water tank can circulate through the electrolyzer and the water tank and can be electrolyzed to generate hydrogen. Alternatively, each simplified disposable instrument may be used for the same purpose (Japanese Patent Laid-Open Nos. 2016-112562, etc.). This instrument houses a plastic bag (a hydrogen-permeable bag such as a polyethylene bag) containing biocompatible liquid in an aluminum bag and a hydrogen generating agent (e.g., metallic calcium, metallic magnesium/cation exchange resin). The hydrogen generating agent is wrapped by, for instance, non-woven fabric (e.g., water vapor-permeable non-woven fabric). The hydrogen generating agent wrapped by non-woven fabric is made wet by using a small amount of water such as water vapor to generate hydrogen. This hydrogen permeates through the plastic bag and is aseptically dissolved, in a nondestructive manner, into the biocompatible liquid.

The hydrogen gas-containing gas and/or the hydrogen-rich biocompatible liquid (e.g., sterilized water, saline, instillation fluids, beverages), which have been prepared using the above apparatus or instrument, may be orally or parenterally administered to subjects with age-related macular degeneration.

Another form of the composition according to the present invention involves a dosage form (e.g., a tablet, a capsule) containing a hydrogen generating agent that is prepared for oral administration (or intake) to a subject and allows for hydrogen generation in the alimentary tract. In this case, the hydrogen generating agent is preferably composed of a safe component approved as, for instance, a food or a food additive.

3. Treatment or Prophylaxis of Age-Related Macular Degeneration

A second aspect of the present invention provides a method for treatment or prophylaxis of age-related macular degeneration in a subject with age-related macular degeneration, comprising administering, to the subject, the above composition according to the present invention.

Preferable examples of a method for administering a composition of the present invention to a subject includes transpulmonary administration such as inhalation and aspiration when hydrogen gas is the active ingredient. Also, preferred is oral administration, intravenous administration (including dripping), or intraocular administration when a hydrogen-dissolved liquid is the active ingredient. At the time of inhalation of gas, the gas can be inhaled and sent from the mouth or nose, via a nasal cannula or mask-type instrument covering the mouth and nose, into the lung and then systemically delivered through blood flow.

Preferably, the hydrogen-dissolved liquid for oral administration may be stored at a low temperature or the cooled liquid or the liquid stored at normal temperature may be administered to a subject. It has been known that hydrogen can be dissolved at a concentration of about 1.6 ppm (1.6 mg/L) into water at normal temperature and pressure and the temperature causes a relatively small difference in solubility. Alternatively, the hydrogen-dissolved liquid may be in a form of instillation fluid, eye drops, or injection solution containing hydrogen gas prepared using, for example, the above nondestructive hydrogen-adding apparatus. In this case, the hydrogen-dissolved liquid may be administered to a subject via a parenteral administration route, such as intravenous administration, intraarterial administration, or intraocular administration.

Single or multiple daily doses (e.g., several doses) of the hydrogen gas-containing gas having the above hydrogen concentration or the hydrogen-dissolved liquid having the above dissolved hydrogen concentration may be given to a subject once or a couple of times (e.g., 2 to 3 times) per day, over a period of, for instance, 1 week to 3 months or more, 1 week to 6 months or more, or 1 year to 3 years or more. The hydrogen gas-containing gas may be administered per dose over, for instance, 10 min to 2 h or more, 20 min to 40 min or more, 30 min to 2 h or more, or 1 h to 3 h or more. In addition, the hydrogen gas-containing gas may be administered transpulmonarily by inhalation or aspiration. In this case, the gas may be administered to a subject under atmospheric pressure conditions or high-pressure conditions, for instance, at a high pressure within a range from more than normal atmospheric pressure (i.e., about 1.013 atm) to 7.0 atm or less such as from 1.02 to 7.0 atm, preferably from 1.02 to 5.0 atm, more preferably from 1.02 to 4.0 atm, and still more preferably from 1.02 to 1.35 atm, that is, in the presence of the hydrogen gas-containing gas having the above hydrogen concentration.

The above high-pressure conditions can be created by using a high-pressure housing (e.g., a capsule) designed to have sufficient strength and be able to pressurize and inject the above hydrogen gas-containing gas (e.g., hydrogen-containing oxygen or air) to create an inside high-pressure atmosphere at more than normal atmospheric pressure and 7.0 atm or less. It is preferable that the shape of the high-pressure housing be resistant to pressure and be thus generally rounded without edges. It is also preferable that the high-pressure housing be made of light-weight and high-strength material. Examples of the material include reinforced plastics, carbon fiber composite materials, titanium alloys, and aluminum alloys. In the above high-pressure housing, each subject may be given the hydrogen gas-containing composition for treatment or prophylaxis of AMD, together with oxygen gas or the air.

As used herein, the term "subject" includes mammals (e.g., primates including humans, pet animals such as dogs and cats, caged animals in zoos). Preferably, the subject is a human.

The above treatment of AMD with molecular hydrogen according to the present invention is characterized in that (1) non-invasive, simple therapy can be implemented on patients with AMD; (2) the treatment is not accompanied by any adverse events; (3) the treatment causes choroidal neovascularization to substantially disappear in AMD; (4) the treatment causes retinal pigment epithelium detachment to be substantially lost; and (5) the treatment results in marked improvement in visual acuity, etc. The case of the Examples described later clearly demonstrates that the characteristics (3), (4), and (5) of the above characteristics, in particular, are due to the treatment with molecular hydrogen as an active ingredient of the composition according to the present invention. This is surprising because, to date, it has been totally unknown that hydrogen administration causes choroidal neovascularization to substantially disappear and retinal pigment epithelium detachment to be substantially lost in AMD.

Further, a composition according to the present invention can be also used for prophylaxis of AMD. Since the eyes are constantly exposed to light, reactive oxygen species are likely to occur. Because of this, it has been pointed out that photooxidative stress may be associated with ocular diseases (e.g., cataract, AMD, glaucoma, diabetes retinopathy) (Non Patent Literatures 3 and 4). It has been known that any of the above exemplified ocular diseases except for diabetes retinopathy is caused by aging. Accordingly, it is considered that the ocular diseases develop because long-term intraocular generation of reactive oxygen species leads to a failure in balance with its scavenging system, so that oxidative stress becomes dominant. The molecular hydrogen, which is an active ingredient of a composition according to the present invention, can scavenge intraocular reactive oxygen species. Thus, the composition of the present invention may be used for preventing the onset of the above ocular diseases including AMD or for preventing recurrence after treatment of the above ocular diseases including AMD.

In the present invention, the composition of the present invention may be just administered to a subject with AMD to effectively treat or prevent AMD. Further, in order to enhance the therapeutic effect of AMD, treatment with another drug for treatment of AMD and/or physical therapy (e.g., a treatment protocol in which choroidal angiogenesis is physically destroyed or suppressed) for treatment of AMD may be combined in the therapy of interest. The administration timing when the composition of the present invention is administered in the above combination therapy is not particularly limited. For instance, in the combination therapy, the composition of the present invention may be administered before implementation of the treatment with another drug for treatment of AMD or the treatment with physical therapy for treatment of AMD, during the administration or implementation, or after the administration or implementation. The Examples described later demonstrated that although treatment with another drug for treatment of AMD (e.g., Lucentis (R)) and treatment with photodynamic therapy (e.g., laser therapy) did not ameliorate the symptoms, this AMD case was markedly ameliorated when a composition of the present invention was administered during or after these treatments.

Examples of another drug for treatment of age-related macular degeneration include the above anti-angiogenic drugs and antioxidants. Examples of the anti-angiogenic drugs include anti-VEGF drugs (e.g., ranibizumab, bevacizumab, aflibercept) and steroid medicines (adrenocortical hormone such as triamcinolone acetonide). These drugs are administered intraocularly (e.g., injected into the vitreous body) in clinical practice. Examples of the antioxidants include substances which are found to have antioxidative actions, such as vitamin A, vitamin C or vitamin E, carotenoids, polyphenols, luteins, anthocyanin, zeaxanthin, and zinc. It is preferable that an antioxidant vitamin and zinc are used in combination. Examples of the other drugs include docosahexaenoic acid (DHA) and eicosapentaenoic acid (EPA), which are considered to suppress the onset of AMD. The above antioxidant and another substance may be administered by suitably including them into eye drops or may be taken orally.

Examples of the combination therapy with treatment with physical therapy for treatment of AMD include a combination of treatment of AMD with a composition of the present invention and laser photocoagulation treatment or photodynamic therapy. To this combination may be further added treatment with the above-mentioned another drug for treatment of AMD.

The laser photocoagulation treatment is a treatment protocol in which neovascularization outside of the fovea is irradiated with laser beam and is burnt. This eliminates macular edema and hemorrhage, thereby capable of suppressing reduced visual acuity.

The photodynamic therapy is a treatment protocol in which a photo-reactive agent (e.g., verteporfin) is injected and laser is then used to occlude and reduce neovascularization. This agent is characteristic of being occluded in neovascularization. Laser irradiation causes a chemical reaction with the agent and the resulting reactive oxygen species in the neovascularization affect and cause formation of blood clots in the neovascularization to occlude blood vessels, thereby reducing the neovascularization.

The treatment or prophylaxis of AMD with a composition of the present invention should be performed based on diagnosis and instructions by an ophthalmologist. When the treatment or prophylaxis of AMD is performed using a composition of the present invention, it is desirable to use a hydrogen gas generator, a hydrogen water generator, or a hydrogen gas-adding apparatus, (e.g., devices such as the above hydrogen gas supply device (or a gaseous hydrogen inhalation device), a hydrogen-adding instrument (or a hydrogen water generator), a nondestructive hydrogen-adding apparatus (e.g., an apparatus for dissolving, in a nondestructive manner, hydrogen gas into a biocompatible liquid such as instillation fluid contained in a hydrogen-permeable bag)), the sufficient therapeutic effect and safety of which have been confirmed.

The treatment or prophylaxis (e.g., recurrence prevention) of AMD should be based on instructions or a treatment regimen of an ophthalmologist. It is preferable to perform treatment of AM with a composition of the present invention, or a combination therapy of treatment of AMD with a composition of the present invention and treatment with another drug for treatment of AMD and/or physical therapy for treatment of AMD.

EXAMPLES

The present invention is further specifically described by referring to Examples below. However, the technical scope of the present invention is not limited to these Examples.

<Example 1>Hydrogen-Mediated Treatment of Age-Related Macular Degeneration (1) Case A patient (man, aged 62) felt itchiness on the left eye in September 2013, took his glasses off, and covered his left eye. When the left eye was covered, the right eye visual field was distorted.

The distortion regarding the right eye was directed from the left to the upper right in the visual field. When the patient saw furniture placed in a room, the width thereof was perceived as about ⅔ of the width. When looking at someone's face, he could not identify who it is.

Next day, he visited an ophthalmologist and the doctor told him that he had serious disease. Later, as a result of fundus angiography, he was diagnosed as (wet) age-related macular degeneration.

The ophthalmologist said that treatment with Lucentis (R) (an anti-VEGF drug, ranibizumab; Novartis Pharma K. K.) was possible but laser therapy was unavailable here. The doctor recommended a general hospital where laser therapy was available, so he visited the general hospital in Joetsu-city (Niigata, Japan).

(2) Treatment 1

In the general hospital, a test and a treatment regimen were provided, and the patient decided to receive positive treatment.

Lucentis (R) was injected in the vitreous body of the patient and the patient received laser therapy after 1 week. After additional 1 month, Lucentis (R) was re-injected.

Since the therapeutic effect appeared, a Lucentis (R) injection interval was gradually increased. After 10 months, the injection was discontinued and only a test was continued. Thereafter, the patient visited the hospital once in three months and his pathological conditions were checked by a test.

Two years later, he received a test result showing that his pathological conditions got worse.

The patient received the same treatment as before, but the treatment outcome was not good. Then, the patient received the second laser therapy, and Lucentis (R) injection approximately once a month.

Although the patient received Lucentis (R) injection in January 2018, a test result was very bad. The doctor recommended that the patient receive another laser therapy if the result of injection in February was bad.

(3) Treatment 2

February 2018, the patient aspirated gaseous hydrogen for about 2 hours per occasion a total of 3 times (with a 7-day interval) by using a gaseous hydrogen inhalation device (MHG-2000 (R); MiZ Company Limited). The hydrogen concentration in MHG-2000 is about 4% by volume (level of hydrogen generated: about 70 ml/min).

After that, the patient received Lucentis (R) injection. One week after the injection, detailed fundus examination was conducted to check his pathological conditions. Then, his choroidal neovascularization was found to degenerate.

During three years before initiation of hydrogen gas inhalation, a situation where no effects of laser therapy and Lucentis (R) injection were observed continued. Hence, the choroidal neovascularization degeneration was determined to be due to the effects of hydrogen aspiration.

Further, a hydrogen water generator Aquela blue (R) (MiZ Company Limited) was used, the generator allowing generation of hydrogen water at a hydrogen concentration of 1.6 ppm (level of hydrogen generated: about 9 ml/500 ml). Then, the patient daily drank 500 ml/morning and 500 ml/night of the water for 1 month.

When the patient received Lucentis (R) injection on Apr. 11, 2018, his pathological conditions were checked. At that time, the symptom of retinal pigment epithelium detachment somewhat remained. However, after one week, the patient was re-examined. Then, the choroidal neovascularization was found to disappear, and the retinal pigment epithelium detachment was also found to be lost. In addition, because the patient aspirated hydrogen and drank hydrogen water, the visual acuity of the eye on the side with age-related macular degeneration was improved from 0.1 to 1.2.

INDUSTRIAL APPLICABILITY

The present invention is useful for amelioration of the symptoms of age-related macular degeneration by treatment.

The invention claimed is:

1. A method for treatment or prophylaxis of age-related macular degeneration in a human with age-related macular degeneration, comprising administering, to the human, a composition comprising an effective amount of molecular hydrogen,
   wherein the composition is in a form of hydrogen gas-containing gas; and
   wherein the administration of the composition is performed through inhalation.

2. The method according to claim 1, wherein a hydrogen concentration in the hydrogen gas-containing gas is more than zero (0) and 18.5% by volume or less.

3. The method according to claim 1, wherein the inhalation is carried out under an atmospheric pressure condition or under a high-pressure condition at from 1.02 to 7.0 atm.

4. The method according to claim 1, wherein the composition is prepared in situ at the time of administration to the human by using a hydrogen gas generator.

5. The method according to claim 1, wherein the age-related macular degeneration is age-related macular degeneration that causes choroidal angiogenesis.

* * * * *